United States Patent
Zhang et al.

(10) Patent No.: US 6,588,251 B2
(45) Date of Patent: Jul. 8, 2003

(54) METHOD FOR CHECKING THE DYNAMIC BEHAVIOR OF A MEASURING SENSOR IN THE EXHAUST TRACT OF AN INTERNAL COMBUSTION ENGINE

(75) Inventors: Hong Zhang, Regensburg (DE); Jürgen Rössler, Regensburg (DE); Corinna Pfleger, Donaustauf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/751,957
(22) Filed: Dec. 29, 2000

(65) Prior Publication Data
US 2001/0002550 A1 Jun. 7, 2001

Related U.S. Application Data

(63) Continuation-in-part of application No. PCT/DE99/01620, filed on Jun. 1, 1999.

(30) Foreign Application Priority Data

Jun. 29, 1998 (DE) .......................... 198 28 929

(51) Int. Cl.⁷ ...................... G01N 33/497; G01M 19/00
(52) U.S. Cl. ..................... 73/23.32; 73/118.1
(58) Field of Search .................. 73/116, 118.1, 73/23.31, 23.32; 60/274–300; 123/672, 676, 688, 691, 697; 340/438, 449

(56) References Cited

U.S. PATENT DOCUMENTS

| 5,235,957 A | 8/1993 | Furuya |
| 5,370,101 A | 12/1994 | Hamburg et al. |
| 5,488,858 A | 2/1996 | Achleitner |
| 6,167,695 B1 * | 1/2001 | Itou et al. ................ 73/118.1 |

FOREIGN PATENT DOCUMENTS

| EP | 0 616 119 A1 | 9/1994 |
| EP | 0 637 684 A1 | 2/1995 |

OTHER PUBLICATIONS

Published International Application No. WO 90/09517 (Schnaibel et al.), dated Aug. 23, 1990.
"Performance of Thick Film NOx Sensor on Diesel and Gasoline Engines" (Kato et al.), dated 1997, Society of Automotive Engineers, Inc., Publication No. 970858, as mentioned on p. 2 of the specification.

* cited by examiner

Primary Examiner—Eric S. McCall
Assistant Examiner—Maurice Stevens
(74) Attorney, Agent, or Firm—Laurence A. Greenberg; Werner H. Stemer; Ralph E. Locher

(57) ABSTRACT

A method is provided for checking the dynamic behavior of a measuring sensor which detects a substance concentration in the exhaust tract of an internal combustion engine operating with excess air, downstream of an NOx storage catalytic converter. A signal from the measuring sensor is monitored during a regeneration phase. When a predetermined signal profile is absent, a faulty dynamic behavior is diagnosed.

8 Claims, 2 Drawing Sheets

METHOD FOR CHECKING THE DYNAMIC BEHAVIOR OF A MEASURING SENSOR IN THE EXHAUST TRACT OF AN INTERNAL COMBUSTION ENGINE

CROSS-REFERENCE TO RELATED APPLICATION

This application is a continuation in part of copending International Application No. PCT/DE99/01620, filed Jun. 1, 1999, which designated the United States.

BACKGROUND OF THE INVENTION

Field of the Invention

The invention relates to a method for checking the dynamic behavior of a measuring sensor which detects at least one substance concentration in the exhaust tract of an internal combustion engine operating with excess air, downstream of an NOx storage catalytic converter which catalytically converts stored NOx by the addition of a reducing agent, in a regeneration phase. The reducing agent is produced by operating the internal combustion engine briefly with a rich air/fuel mixture (lambda<1).

Internal combustion engines with lean combustion are employed with increasing frequency to reduce the fuel consumption of spark ignition internal combustion engines even further. It is necessary to have special exhaust gas retreatment in such internal combustion engines in order to meet the required exhaust gas emission limit values. NOx storage catalytic converters are used for that purpose. Those Nox storage catalytic converters, by virtue of their coating, are capable of absorbing NOx compounds from the exhaust gas which occur in a storage phase during lean combustion. The absorbed or stored NOx compounds are converted during a regeneration phase, by the addition of a reducing agent, into harmless compounds. CO, $H_2$ and HC (hydrocarbons) may be used as reducing agents for lean-operated spark ignition internal combustion engines. Those agents are produced by briefly operating the internal combustion engine with a rich mixture and are made available to the NOx storage catalytic converter as exhaust gas components. As a result, the stored NOx compounds in the catalytic converter are broken down.

A measuring sensor is provided downstream of the NOx storage catalytic converter in the exhaust tract for detecting at least one substance concentration, in order to control the regeneration and storage phases or to check the NOx storage catalytic converter. Measuring sensors which emit an NOx signal representing the NOx concentration are normally used. Such a measuring sensor is known, for example, from a publication entitled "Performance of Thick Film Nox Sensor on Diesel and Gasoline Engines", by N. Kato, Y. Hamada and H. Kurachi, in Society of Automotive Engineers, Publication No. 970858.

Self-diagnosis (On Board Diagnosis=OBD) of the entire exhaust gas retreatment system is increasingly demanded to ensure that the required exhaust gas emission limit values are adhered to over the entire service life of such an internal combustion engine. Such OBD is necessary, in particular, for the dynamic behavior of a measuring sensor that is used. In that case, a slowdown in the response of the measuring sensor should be able to be detected and, if there is an inadequate dynamic behavior, a faulty measuring sensor should be able to be diagnosed.

In contrast to a lambda probe disposed upstream of a catalytic converter, the exhaust gas downstream of a catalytic converter, in particular an NOx storage catalytic converter, normally does not have any pronounced substance concentration fluctuations. Therefore, it is difficult to recognize a slowed-down response of a measuring sensor.

SUMMARY OF THE INVENTION

It is accordingly an object of the invention to provide a method for checking the dynamic behavior of a measuring sensor disposed downstream of an NOx storage catalytic converter in the exhaust tract of an internal combustion engine for detecting a substance concentration, which overcomes the hereinafore-mentioned disadvantages of the heretofore-known methods of this general type.

With the foregoing and other objects in view there is provided, in accordance with the invention, a method for checking the dynamic behavior of a measuring sensor detecting at least one substance concentration, which comprises providing an internal combustion engine operating with excess air and producing a reducing agent by operating briefly with a rich air/fuel mixture. An exhaust tract is provided for the internal combustion engine. An NOx storage catalytic converter is placed in the exhaust tract for catalytically converting stored Nox by an addition of the reducing agent in a regeneration phase. The measuring sensor is placed downstream of the NOx storage catalytic converter in the exhaust tract for emitting a measuring sensor signal representing a substance concentration. A rate of change of at least one substance-concentration is monitored during the regeneration phase. A faulty dynamic behavior of the measuring sensor signal is diagnosed when the rate of change is not reproduced with sufficient edge steepness by the measuring sensor signal.

The invention proceeds from the knowledge that, in the regeneration phase of the NOx storage catalytic converter, substance concentration changes occur with predetermined rates of change. Thus, the dynamics of the measuring sensor can be checked by monitoring the rate of change of a substance concentration. It is thereby possible to check the dynamics of a plurality of signals from a measuring sensor which represent different substance concentrations, depending on the embodiment of the method according to the invention. An NOx signal representing the NOx concentration, a lambda signal representing the lambda value and an $O_2$ signal representing the oxygen concentration, are particularly relevant.

It is therefore important that the rate of change of one or more substance concentrations in the regeneration phase be monitored, since the changes in the substance concentration are then caused by reactions in the NOx storage catalytic converter itself or changes produced in the lambda value appear with sufficient amplitude at the measuring sensor. Such dynamics cannot be produced at any other operating point, since, in a lambda≈1 operating mode, the fluctuations in the substance concentration or in the lambda value downstream of the catalytic converter are too low or are damped by the catalytic converter. In normal operation, this damping makes it impossible to produce substance concentration changes with a high rate of change in order to check the measuring sensor dynamics through the use of mixture changes while the internal combustion engine is in operation.

Other features which are considered as characteristic for the invention are set forth in the appended claims.

Although the invention is illustrated and described herein as embodied in a method for checking the dynamic behavior of a measuring sensor in the exhaust tract of an internal combustion engine, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
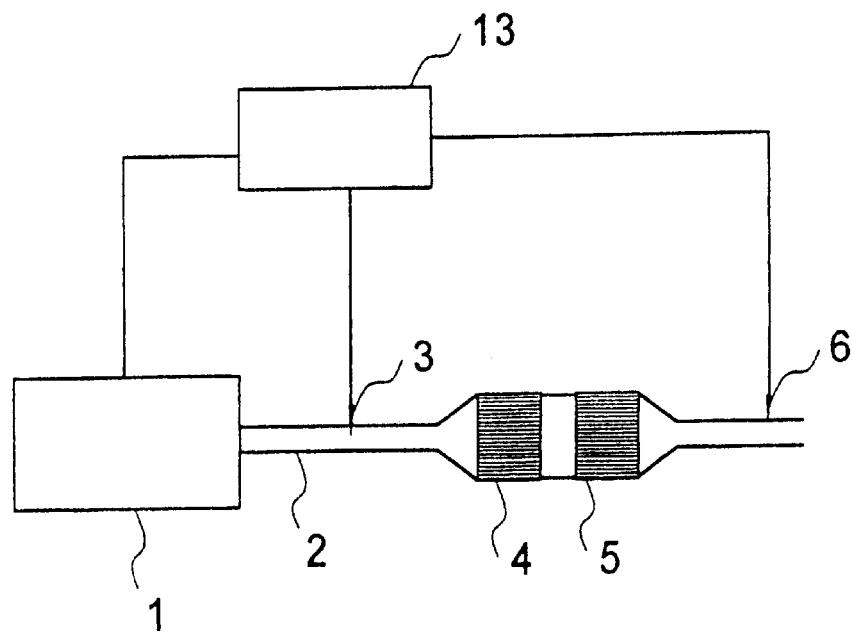
FIG. 1 is a schematic and block diagram of an exhaust tract of an internal combustion engine with an exhaust gas retreatment system.

Referring now to the figures of the drawings in detail and first, particularly, to FIG. 1 thereof, there is seen an internal combustion engine 1 having an exhaust tract 2 with an exhaust gas retreatment system which is to have OBD capabilities. A three-way pre-catalytic converter 4 and an NOx storage catalytic converter 5 are disposed in the exhaust tract 2 of the internal combustion engine 1. A single catalytic converter exhibiting both properties is also possible. A pre-catalytic converter lambda probe 3 is located upstream of these two catalytic converters and an NOx measuring sensor 6 is located downstream thereof. The operation of the internal combustion engine 1 and of the exhaust gas retreatment system is controlled by an operational control unit 13 which, inter alia, receives measurement values from the pre-catalytic converter lambda probe 3 and the NOx measuring sensor 6 and carries out the OBD.

The dynamic behavior of the NOx measuring sensor 6 is to be checked in this OBD. In addition to emitting the NOx signal representing the NOx concentration, an NOx measuring sensor 6 also emits a lambda signal representing the lambda value and an $O_2$ signal representing the oxygen concentration. The dynamic behavior of both signals is to be checked.

As is known, the internal combustion engine 1 may be operated in such a way that the lambda value executes a defined oscillation about lambda=1 at the pre-catalytic converter lambda probe 3. According to the prior art, this oscillation is then used to check the dynamic behavior of the pre-catalytic converter lambda probe 3. However, this procedure is not suitable for the NOx measuring sensor 6, since the latter is located downstream of the three-way pre-catalytic converter 4 and of the NOx storage catalytic converter 5 and the oscillation about lambda=1 is markedly damped by the two catalytic converters. Therefore, it is not possible to recognize a slowed-down response or inadequate dynamic behavior of the NOx measuring sensor 6.

Figure 2:
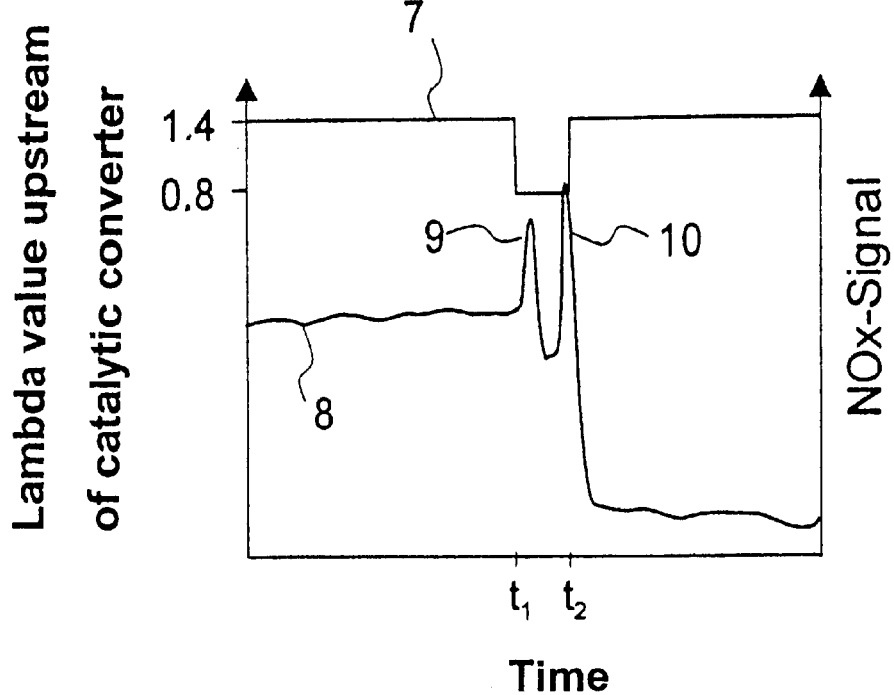
FIG. 2 is a diagram showing a time profile of an NOx signal of an NOx measuring sensor disposed downstream of an NOx storage catalytic converter, during a regeneration phase.

It is, however, possible to check the dynamic behavior of the NOx measuring sensor 6 in a regeneration phase of the NOx storage catalytic converter 5. In these regeneration phases, the NOx stored by the NOx storage catalytic converter 5 in the lean operating mode of the internal combustion engine 1 is converted. A switch is made from lambda=1 or from lambda>1 to a mixture of defined richness with, for example, lambda=0.8 for this regeneration. Such a regeneration phase is illustrated in FIG. 2. A curve 7 shows a time profile of the lambda value of an untreated exhaust gas. As can be seen clearly, at the start of the regeneration phase, a switch is made from lambda≈1.4 to lambda=0.8 at a time point $t_1$. At the end of the regeneration phase, the original lambda value of approximately 1.4 is set again at a time point $t_2$. A curve 8 illustrates a time profile of the NOx signal from a fully operational NOx measuring sensor. NOx is released briefly in or through the regeneration phase. This NOx originating from desorption of the NOx storage catalytic converter can be recognized clearly from a desorption peak 9 in the NOx signal from the NOx measuring sensor 6. If the NOx signal from the NOx measuring sensor 6 does not reproduce one or both edges of this desorption peak 9 in a regeneration phase with sufficient bandwidth, that is to say with inadequate edge steepness, a faulty dynamic behavior of the NOx measuring sensor 6 with regard to NOx must be diagnosed.

Ammonia ($NH_3$) is also formed for a short time toward the end of the regeneration phase. Since the NOx measuring sensor 6 exhibits cross-sensitivity of the NOx signal to $NH_3$, as is known from the publication cited above, an $NH_3$ peak 10 is detected in the NOx signal toward the end of the regeneration phase. If one or both edges of the $NH_3$ peak 10 are not reproduced with sufficient edge steepness, a faulty dynamic behavior of the NOx measuring sensor 6 may likewise be diagnosed.

The peaks 9 and 10 may also coincide, depending on the NOx storage catalytic converter 5 and the measuring sensor 6 being used.

It may be pointed out that the desorption peak 9 and the $NH_3$ peak 10 occur as a result of reactions in the NOx storage catalytic converter 5 itself. It is virtually impossible to produce such peaks through the use of mixture changes during normal operation since, for example, NOx jumps produced by the internal combustion engine 1 are damped to a great extent by the catalytic converters 4, 5.

Figure 3:
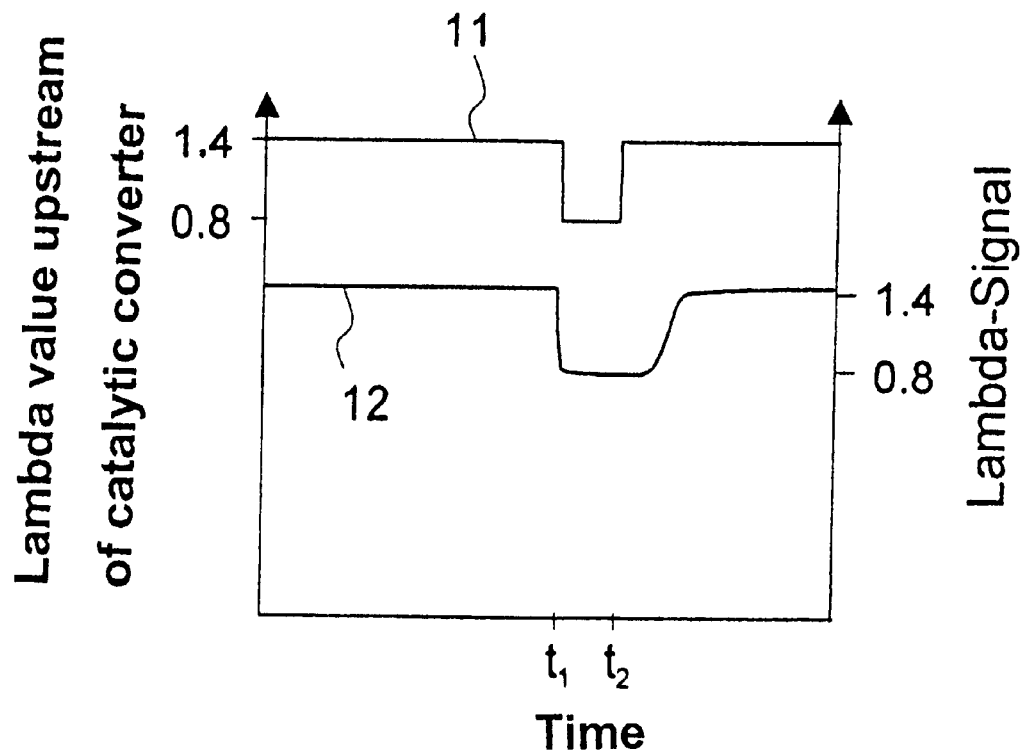
FIG. 3 is a diagram showing a time profile of a lambda signal of such a measuring sensor which, in addition to the NOx signal, also emits a lambda signal representing a lambda value.

If the NOx measuring sensor 6 additionally supplies a lambda signal or an $O_2$ signal as well, the dynamic behavior thereof can likewise be checked during the regeneration phase, as is illustrated in FIG. 3. In a similar way to the curve 7 of FIG. 2, a curve 11 shows the time profile of the lambda value of the untreated exhaust gas during a regeneration phase. A curve 12 reproduces the time profile of the lambda signal from a fully operational NOx measuring sensor 6. When the mixture is switched to lambda≈0.8 at the time point $t_1$ in the regeneration phase, the dynamics of the lambda signal from the NOx measuring sensor 6 can be checked from this lambda jump into the rich range. If such a lean/rich jump is not reproduced with sufficient bandwidth or edge steepness by the lambda signal from the NOx measuring sensor 6, a faulty dynamic behavior of a lambda signal from the NOx measuring sensor 6 may be diagnosed. The rich/lean jump at the end of the regeneration phase may, of course, also be used for diagnosis.

The advantage of utilizing a jump in the lambda value of the untreated exhaust gas at the start of a regeneration phase is that such a lambda jump has a markedly higher amplitude than an oscillation of the lambda value upstream of the catalytic converters 4, 5 which occurs in normal operation and which is, of course, also greatly damped by the catalytic converters 4, 5. A sharp change in the lambda value is thus available in the regeneration phase at the place of installation of the NOx measuring sensor 6 downstream of the catalytic converters 4 and 5. This change may be utilized in order to check the dynamic behavior of the lambda signal or of the $O_2$ signal from the NOx measuring sensor 6.

We claim:

1. In a method for checking the dynamic behavior of a measuring sensor detecting at least one substance concentration, the improvement which comprises:
    providing an internal combustion engine operating with excess air and producing a reducing agent by operating briefly with a rich air/fuel mixture;
    providing an exhaust tract for the internal combustion engine;
    placing an NOx storage catalytic converter in the exhaust tract for catalytically converting stored NOx by addition of the reducing agent in a regeneration phase;
    placing the measuring sensor downstream of the NOx storage catalytic converter in the exhaust tract for emitting a measuring sensor signal representing a substance concentration, the measuring sensor signal having peaks with edges as a result of changes of the substance concentration during the regeneration phase;
    monitoring at least one of the edges of the measuring sensor signal during the regeneration phase; and
    diagnosing a faulty dynamic behavior of the measuring sensor signal upon at least one of the edges of the measuring sensor signal not having sufficient steepness.

2. The method according to claim 1, which further comprises:
    monitoring a substance concentration change occurring in the form of an NOx desorption peak during the regeneration phase;
    emitting an NOx signal representing a NOx concentration in the exhaust gas, with the measuring sensor; and
    monitoring the NOx signal to determine if at least one edge of the NOx desorption peak is reproduced with sufficient edge steepness.

3. The method according to claim 1, which further comprises:
    monitoring a substance concentration change occurring in the form of an $NH_3$ peak toward an end of the regeneration phase;
    emitting an NOx signal representing the NOx concentration in the exhaust gas and exhibiting cross-sensitivity to $NH_3$, with the measuring sensor; and
    monitoring the NOx signal to determine if at least one edge of the $NH_3$ peak is reproduced with sufficient edge steepness.

4. The method according to claim 2, which further comprises:
    monitoring a substance concentration change occurring in the form of an $NH_3$ peak toward an end of the regeneration phase;
    emitting an NOx signal representing the NOx concentration in the exhaust gas and exhibiting cross-sensitivity to $NH_3$, with the measuring sensor;
    monitoring the NOx signal to determine if at least one edge of the $NH_3$ peak is reproduced with sufficient edge steepness; and
    causing the NOx desorption peak and the $NH_3$ peak to coincide during the monitored substance concentration change.

5. The method according to claim 1, which further comprises:
    monitoring a substance concentration change occurring as a jump of a lambda value from a lean to a rich mixture at a start of the regeneration phase;
    emitting a lambda signal representing the lambda value in the exhaust gas, with the measuring sensor; and
    monitoring the lambda signal to determine if the jump is reproduced with sufficient edge steepness.

6. The method according to claim 1, which further comprises:
    monitoring a substance concentration change occurring as a jump of a lambda value from a rich to a lean mixture at an end of the regeneration phase;
    emitting a lambda signal representing the lambda value in the exhaust gas, with the measuring sensor; and
    monitoring the lambda signal to determine if the jump is reproduced with sufficient edge steepness.

7. The method according to claim 1, which further comprises:
    monitoring a substance concentration change occurring as a jump of an oxygen concentration from a lean to a rich mixture at a start of the regeneration phase;
    emitting an $O_2$ signal representing the oxygen concentration in the exhaust gas, with the measuring sensor; and
    monitoring the $O_2$ signal to determine if the jump is reproduced with sufficient edge steepness.

8. The method according to claim 1, which further comprises:
    monitoring a substance concentration change occurring as a jump of an oxygen concentration from a rich to a lean mixture at an end of the regeneration phase;
    emitting an $O_2$ signal representing the oxygen concentration in the exhaust gas, with the measuring sensor; and
    monitoring the $O_2$ signal to determine if the jump is reproduced with sufficient edge steepness.

* * * * *